United States Patent
Philip et al.

(10) Patent No.: US 11,896,805 B2
(45) Date of Patent: Feb. 13, 2024

(54) CONNECTED HEALTH PLATFORM INCLUDING NEEDLE-FREE INJECTOR SYSTEM

(71) Applicant: PORTAL INSTRUMENTS, INC., Cambridge, MA (US)

(72) Inventors: Mark Philip, Boston, MA (US); Patrick Armand Anquetil, Cambridge, MA (US); Ian Hunter, Lincoln, MA (US)

(73) Assignee: PORTAL INSTRUMENTS, INC., Cambridge, MA (US)

( * ) Notice: Subject to any disclaimer, the term of this patent is extended or adjusted under 35 U.S.C. 154(b) by 571 days.

(21) Appl. No.: 16/823,043

(22) Filed: Mar. 18, 2020

(65) Prior Publication Data
US 2020/0219612 A1 Jul. 9, 2020

Related U.S. Application Data

(63) Continuation of application No. 15/368,145, filed on Dec. 2, 2016, now abandoned.

(60) Provisional application No. 62/368,038, filed on Jul. 28, 2016.

(51) Int. Cl.
*G16H 40/60* (2018.01)
*A61M 5/30* (2006.01)
*G16H 30/40* (2018.01)

(52) U.S. Cl.
CPC .............. *A61M 5/30* (2013.01); *G16H 30/40* (2018.01); *G16H 40/60* (2018.01); *A61M 2205/3584* (2013.01)

(58) Field of Classification Search
CPC .. A61M 2005/1726; A61M 2205/3306; A61M 2205/332; A61M 2205/3331; A61M 2205/3358; A61M 2205/3368; A61M 2205/3584; A61M 5/1723; G06Q 50/22
See application file for complete search history.

(56) References Cited

U.S. PATENT DOCUMENTS

| | | |
|---|---|---|
| 5,354,273 A | 10/1994 | Hagen |
| 5,383,851 A | 1/1995 | McKinnon, Jr. et al. |
| 5,536,249 A | 7/1996 | Castellano et al. |
| 9,550,029 B2 | 1/2017 | Boyden et al. |

(Continued)

FOREIGN PATENT DOCUMENTS

| | | | | |
|---|---|---|---|---|
| CN | 103269737 A | * | 8/2013 | ............ A61M 5/30 |
| WO | WO-2015171964 A1 | * | 11/2015 | ............ A61M 5/007 |

*Primary Examiner* — William R Carpenter
(74) *Attorney, Agent, or Firm* — Lando & Anastasi, LLP (57) ABSTRACT

A needle-free injector system includes a needle-free injector configured to deploy a dose of a treatment to a patient as an injection event, a gyroscope configured to monitor an orientation of the needle-free injector during the injection event, and a processor configured to perform steps of detecting that an actuator of the needle-free injector has deployed the dose in the injection event, monitoring a signal from the gyroscope during the injection event, determining an orientation of the needle-free injector during the injection event based on the signal from the gyroscope, determining whether the injection event was a treatment event including a successful delivery of the dose to the patient based on the orientation of the needle-free injector during the injection event, and transmitting information regarding the injection event to a server.

23 Claims, 6 Drawing Sheets

(56) References Cited

U.S. PATENT DOCUMENTS

| | | |
|---|---|---|
| 10,568,575 B2 | 2/2020 | Martin et al. |
| 2002/0188419 A1* | 12/2002 | Slate ................ A61M 5/20 128/DIG. 13 |
| 2003/0000524 A1 | 1/2003 | Anderson et al. |
| 2003/0005831 A1 | 1/2003 | Hansen et al. |
| 2003/0072058 A1 | 4/2003 | Jespersen |
| 2005/0131342 A1 | 6/2005 | Haar et al. |
| 2005/0192557 A1 | 9/2005 | Brauker et al. |
| 2009/0216182 A1* | 8/2009 | Lauchard ........... H03K 17/955 604/65 |
| 2010/0174225 A1* | 7/2010 | Pesach ................. A61M 5/31 604/113 |
| 2011/0196306 A1 | 8/2011 | De La Huerga |
| 2011/0245776 A1 | 10/2011 | Kendall |
| 2012/0089114 A1 | 4/2012 | Hemond et al. |
| 2014/0142507 A1 | 5/2014 | Armes |
| 2014/0200511 A1 | 7/2014 | Boyden et al. |
| 2014/0322683 A1* | 10/2014 | Baym ................. G16H 20/13 340/5.6 |
| 2014/0371682 A1 | 12/2014 | Bengtsson et al. |
| 2016/0030683 A1 | 2/2016 | Taylor et al. |
| 2017/0080154 A1 | 3/2017 | Mudd et al. |
| 2017/0266370 A1* | 9/2017 | Cerman ........... A61M 5/14248 |
| 2018/0056004 A1 | 3/2018 | Gamliel |

\* cited by examiner

CONNECTED HEALTH PLATFORM INCLUDING NEEDLE-FREE INJECTOR SYSTEM

CROSS REFERENCE TO RELATED APPLICATIONS

This application claims priority under 35 U.S.C. § 120 to U.S. patent application Ser. No. 15/368,145, titled "CONNECTED HEALTH PLATFORM INCLUDING NEEDLE-FREE INJECTOR SYSTEM," filed Dec. 2, 2016, which claims priority under 35 U.S.C. § 119(e) to U.S. Provisional Application Ser. No. 62/368,038, titled "CONNECTED HEALTH PLATFORM INCLUDING NEEDLE-FREE INJECTOR SYSTEM," filed Jul. 28, 2016, which are incorporated herein by reference in their entirety.

BACKGROUND

Technical Field

The application generally relates to needle-free injection systems for administering medicine, and more particularly, in one aspect, to systems and methods for improving compliance with prescribed treatment regimens.

Background

The failure of patients to satisfactorily comply with treatment regimens for a particular disorder may lead to less optimal outcomes in treating the disorder, which in turn leads to increased costs to the patient, medical care provider, and payer (e.g., insurance company). Non-compliance leads to additional care requirements in the future, as well as the waste of expensive medications not being administered. On the other hand, higher levels of compliance may generally lead to better outcomes for disorders requiring such treatments. Better outcomes will typically reduce average costs for the patient, medical care provider, and payer.

To the extent compliance or non-compliance is not apparent from a medical outcome, it must currently be self-reported by the patient. Yet patients may be inaccurate reporters due to memory issues, mistake, or bias. Even when patients provide accurate compliance information to medical professionals, the infrequency of visits between patients and care providers may allow long periods of non-compliance to occur before an issue is discovered.

SUMMARY

Aspects of the present disclosure relate to a medical device system that includes a medical treatment device, for example, a needle-based or needle-free injector such as an auto-injector, jet injector, or the like. The medical treatment device has at least one sensor configured to detect, using the at least one sensor, a degree to which a patient has administered a treatment using the medical treatment device, and configured to transmit information to a server regarding the administration of the treatment; and the server configured to communicate, to a device associated with the patient, a message regarding the administration of the treatment.

Needle-free injection systems offer advantages over needle-based injectors in some applications, including more consistent injections, safer and easier use and maintenance of the injector, and reduced patient discomfort during injections. Yet one issue with traditional needle-free and needle-based injectors is the inability to satisfactorily monitor and influence user compliance. Therefore, according to one aspect, a needle-free injector system includes a needle-free injector having at least one sensor configured to detect, using the at least one sensor, a degree to which a patient has administered a treatment using the needle-free injector, and configured to transmit information to a server regarding the administration of the treatment; and the server configured to communicate, to a device associated with the patient, a message regarding the administration of the treatment. In one embodiment, the device associated with the patient is at least one of a mobile device, a computer, a display terminal, and a television. In another embodiment, the device associated with the patient is a device of an individual other than the patient. In yet another embodiment, the message is a reminder regarding the treatment. In still another embodiment, the message is a question relating to at least one of the treatment, the patient's well-being, and the user's health, wherein the server is further configured to receive, from the device associated with the patient, a response to the at least one question.

In one embodiment, the message is stimulation for the patient to administer the treatment. In another embodiment, the needle-free injector is configured to be communicatively coupled to a disposable device preloaded with a dose of a drug. In a further embodiment, the needle-free injector includes a handheld injector; and a base unit communicatively coupled to the handheld injector and to the server. In another embodiment, the needle-free injector further includes a temperature conditioning element configured to change a temperature of a drug dose administered in the treatment.

In yet another embodiment, the at least one sensor comprises at least one of a pressure sensor, a capacitive sensor, an accelerometer, a gyroscope, and a thermometer. In a further embodiment, the needle-free injector determines, from the gyroscope, that the needle-free injector is oriented in a suitable direction prior to administering the treatment.

In one embodiment, the needle-free injector further includes at least one second sensor configured to detect an ambient condition proximal to the needle-free injector. In a further embodiment, the ambient condition is an amount of atmospheric moisture.

In another embodiment, the system further includes a network interface configured to communicate with a third party system associated with at least one of a healthcare professional, a pharmacy, an insurer, and a treatment supplier, wherein the server is configured to communicate, to the third party system, information regarding the patient's compliance in administering the treatment. In another embodiment, the system further includes a network interface configured to communicate with a third party system associated with a supplier of the needle-free injector, wherein the server is configured to communicate, to the third party system, information regarding the performance of the needle-free injector. In yet another embodiment, the needle-free injector further includes a network interface and is configured to receive, via the network interface, information from at least one computer application associated with the patient. In a further embodiment, the information from the at least one computer application includes at least one of activity information, diet information, weight information, and physiological information.

In another embodiment, the server is further configured to receive, for a plurality of treatment events over a period of time, a degree to which the patient has administered the plurality of treatment events, and determine a level of compliance of the patient for the plurality of treatment events. In a further embodiment, the server is further configured to determine a target level of compliance of the patient for the plurality of treatment events, and modify a parameter of a subsequent treatment event based on the level of compliance and the target level of compliance. In a still further embodiment, the target level of compliance correlates to an enhanced outcome for a condition being treated by the treatment event.

In another embodiment, the at least one sensor monitors a physical parameter associated with an administration of the treatment. In a further embodiment, the needle-free injector is further configured to determine, using the at least one sensor, a first measurement of a physical parameter of a treatment site on a body of the patient prior to the treatment. In a still further embodiment, the needle-free injector is further configured to determine, using the at least one sensor, a second measurement of the physical parameter of the treatment site on the body of the patient subsequent to the treatment.

According to another aspect, a method of determining patient compliance with a treatment regimen includes detecting a potential treatment event by a needle-free injector system; measuring, using at least one sensor proximal to a treatment site on a body of a patient, at least one physical parameter; and determining, using the measurement of the at least one physical parameter, a level of compliance of the patient for the potential treatment event. According to a further embodiment, the method further includes communicating, to a device associated with the patient, information about the patient's level of compliance in the treatment event. According to a still further embodiment, the method further includes receiving, from the device associated with the patient, a characterization by the patient of the information about the patient's compliance in the treatment event.

According to one embodiment, determining, using the measurement of the at least one physical parameter, the level of compliance of the patient for the potential treatment event includes determining, using a plurality of measurements of the at least one physical parameter taken over a period of time, the level of compliance of the patient for a plurality of potential treatment events. According to a further embodiment, the method further includes determining a target level of compliance of the patient for the plurality of potential treatment events; and modifying a parameter of a second potential treatment event based on the level of compliance and the target level of compliance. According to a still further embodiment, the target level of compliance correlates to an enhanced outcome for a condition being treated by the potential treatment.

According to another embodiment, measuring, using the at least one sensor proximal to the treatment site on the body of the patient, the at least one physical parameter includes determining a first measurement of a physical characteristic of the treatment site on the body of the patient prior to the potential treatment event; and determining a second measurement of the physical characteristic of the treatment site on the body of the patient subsequent to the potential treatment event. According to yet another embodiment, the at least one physical parameter is a skin temperature of a region proximal to the treatment site. According to another embodiment, at least one possible physical parameter is tenting of a region proximal to the treatment site.

According to one embodiment, at least one sensor comprises at least one of a pressure sensor, a capacitive sensor, an accelerometer, and a thermometer. According to another embodiment, the method further includes selecting, with reference to a plurality of defined treatment protocols, at least one physical parameter; and determining, with reference to the plurality of defined treatment protocols, an acceptable measurement range of the at least one physical parameter. According to yet another embodiment, the method further includes determining a first measurement of a physical characteristic of the treatment site on the body of the patient prior to the potential treatment event; and modifying at least one parameter for the potential treatment event responsive to the first measurement of the physical characteristic of the treatment site being outside a defined range. According to a further embodiment, the at least one parameter includes at least one of a dosage amount, dosage duration, or dosage schedule.

According to another embodiment, determining, using the measurement of the at least one physical parameter, the level of compliance of the patient for the potential treatment event includes receiving information from at least one computer application associated with the patient. According to a further embodiment, the information from the at last one computer application includes at least one of activity information, diet information, weight information, and physiological information.

According to another aspect, a method for facilitating compliance in administering a treatment includes providing, to a patient, a needle-free injector having at least one sensor configured to detect, using the at least one sensor, a degree to which the patient has administered a treatment using the needle-free injector, and configured to transmit information regarding the administration of the treatment; receiving from the needle-free injector, information regarding the administration of the treatment; and communicating, to a device associated with the patient, a message regarding the patient's compliance in administering the expected treatment.

According to another aspect, a needle-free injector system includes a needle-free injector unit having at least one sensor and configured to detect, using the at least one sensor, a degree to which a patient has administered an expected treatment using the needle-free injector unit, and further configured to provide information to be transmitted to a server regarding the administration of the expected treatment; and the server configured to communicate, to a device associated with the patient, a message about the patient's compliance in administering the expected treatment. According to a further embodiment, the needle-free injector unit is further configured to be communicatively coupled to the device associated with the patient, and wherein the device associated with the patient is configured to transmit information to the server regarding the administration of the expected treatment. According to a still further embodiment, the device associated with the patient is a mobile device of the patient. According to yet a further embodiment, the needle-free injector unit includes a disposable device preloaded with a dose of a drug.

BRIEF DESCRIPTION OF DRAWINGS

Various aspects of at least one embodiment are discussed below with reference to the accompanying figures, which are not intended to be drawn to scale. The figures are included to provide an illustration and a further understanding of the various aspects and embodiments, and are incorporated in and constitute a part of this specification, but are not intended as a definition of the limits of any particular embodiment. The drawings, together with the remainder of the specification, serve to explain principles and operations of the described and claimed aspects and embodiments. In the figures, each identical or nearly identical component that is illustrated in various figures is represented by a like numeral. For purposes of clarity, not every component may be labeled in every figure. In the figures:

DESCRIPTION

According to one or more embodiments, methods and systems are provided for improving compliance with a drug treatment regimen using a needle-free injector system. A needle-free injector is configured to inject a medicine at a treatment site on the patient's body using an actuator. The injector is configured to receive a cartridge or other structure holding one or more doses of medicine. One or more sensors are located on the injector such that, when the injector is in position to inject the treatment at the treatment site, the one or more sensors are located at or near the treatment (i.e., injection) site.

The sensors may include one or more of a pressure sensor, a capacitive sensor, and a thermometer. The sensors are configured to detect any of a number of physiological parameters of a patient before, during, and/or after the injector has dispensed a dose of medicine. For example, a thermometer sensor may continuously monitor the temperature of a patient's skin at or near the treatment site, and may take temperature readings from before and after an injection event. It may be known that the skin at the injection site grows flush or warm in response to an injection. By monitoring the temperature at the treatment site to see if the temperature rises after the injection event, the likelihood that the injection was successfully delivered to the patient can be determined, or alternately, the likelihood that the drug was unsuccessfully delivered elsewhere (such as injected into an inanimate object or into the air). As another example, a capacitive sensor may be used to determine the capacitance of the patient's skin at the treatment site; if the capacitance is within an expected range for human skin, it can be determined whether the injection should be initiated.

Ambient sensors may also be provided for detecting ambient or situational characteristics of the environment in which the injector is located. Such sensors may include an accelerometer, a gyroscope, an ambient thermometer, and an injectate thermometer. For example, a gyroscope sensor may be used to determine that the injector is oriented correctly before the injection is initiated. As still another example, an accelerometer sensor may be used to determine that the injector remained substantially motionless relative to the patient during the injection, but with enough slight motion detected to confirm that the injection was applied to the patient (as opposed to an inanimate object).

The injector may include one or more separable components, and some components may be battery-powered to make the device more portable and easy to use. For example, the injector may include a battery-powered actuator unit for performing the injection, and a base unit for charging the battery of the actuator unit.

The injector communicates with a server, which may be part of a cloud computing network. The injector may send physiological data, as well as data about injections and other events, to the server. The injector and/or the server may use that data to determine the patient's compliance with a treatment regimen. For example, the duration of the injection event and the physiological data may be used to determine what portion of the full dose of the drug was administered to the patient.

The injector and/or the server may be configured to communicate with a device associated with the patient. For example, the server may send an email or SMS message to the patient's mobile device (e.g., smartphone or tablet) or computer, or may cause an application running on the mobile device to display a message to the patient. The message may provide information about the patient's compliance with the treatment regimen. For example, if a scheduled injection is not administered, the patient may be reminded to administer the injection. Similarly, the patient may receive confirmation that an injection was successful, or may be asked to confirm that the injection was successful. The message may also provide encouragement or motivation to the patient to continue complying with a treatment regimen, such as by including the patient's compliance statistics over a period of time.

The patient may also be presented with a user interface, which can be used to receive biographical information from the patient as part of the configuration of the device, such as the patient's age, gender, medical conditions, lab parameters, and currently prescribed or contraindicated medications. In some embodiments, the user interface presented to the patient may ask one or more questions to determine the compliance with the treatment regimen, or to determine the success of the treatment regimen. For example, the patient may be asked about current or recent pain levels, symptoms, diet, activity level, or the like. Pull down menus may provide a number of present answer options from which the patient may choose. The sequence of displays, questions, and input parameters may be selected and configured based on the condition being treated, and may be adaptive based on answers to previous questions. For example, where the patient indicates some amount of pain is currently being experienced, additional questions may be posed regarding the location, intensity, and duration of the pain.

In some embodiments, a human figure may be displayed, with the user interface configured to receive input from the patient regarding the location and intensity of the pain. For example, the patient may be prompted to touch on the portion of the user interface displaying the region of the human figure where the patient is currently experiencing pain, and to touch for a duration proportional to the intensity of the pain. For example, a patient might touch the leg of the human figure for a short period of time (e.g., 0.5 seconds) if the pain is of relatively low intensity, but might hold the touch for a longer period of time (e.g., 3 seconds) if the pain is of higher intensity. If, alternatively, the patient indicates that minimal or no pain is currently being experienced, those additional pain-related questions may not be presented to the patient.

Information obtained from other sources may also be used to determine compliance. For example, information from an activity tracking app on the user's mobile device may be accessed to determine if the user's activity level is appropriate for the treatment regimen. Diet information may be similarly used to determine compliance.

Alternately, the device associated with the patient may be a device of someone known to the patient, such as a caregiver, family member, neighbor, friend, or the like. In some cases, there may be multiple devices associated with the patient, with different devices receiving messages for various levels of compliance with a treatment regimen. For example, the patient's own device may receive a notification that a single injection was missed within the past hour. If subsequent scheduled injections are also missed, messages may also be sent to a device of the patient's caregiver.

The injector may also communicate directly with the device associated with the patient, such as by a Bluetooth or Wifi connection. Information from the at least one sensor may be provided by the injector to the user device, which may include an application configured to determine compliance information and transmit it to the server.

The server may also send information about the device and the patient's compliance to one or more third parties over a network. For example, information regarding the performance of the injector may be sent to the manufacturer of the injector and/or the medication cartridge to allow for troubleshooting or other diagnostics of the injector. As another example, information about the patient's compliance with a treatment regimen may be sent to the patient's healthcare professional (e.g., physician), hospital, payer (e.g., medical insurance company), a pharmaceutical company, a pharmacy, or others. Such information may be sent by mail or other message format, may be provided via an application programming interface (API) call, or may be provided in a database format or directly loaded into a database.

Events relating to the injector may be logged or otherwise tracked. For example, the date, time, and status of an injection event may be tracked. Software updates to the injector, or periods during which the batter is charged, may also be tracked. Self-testing, diagnostics, provisioning, and shipping events of the injector may also be tracked.

Figure 1:
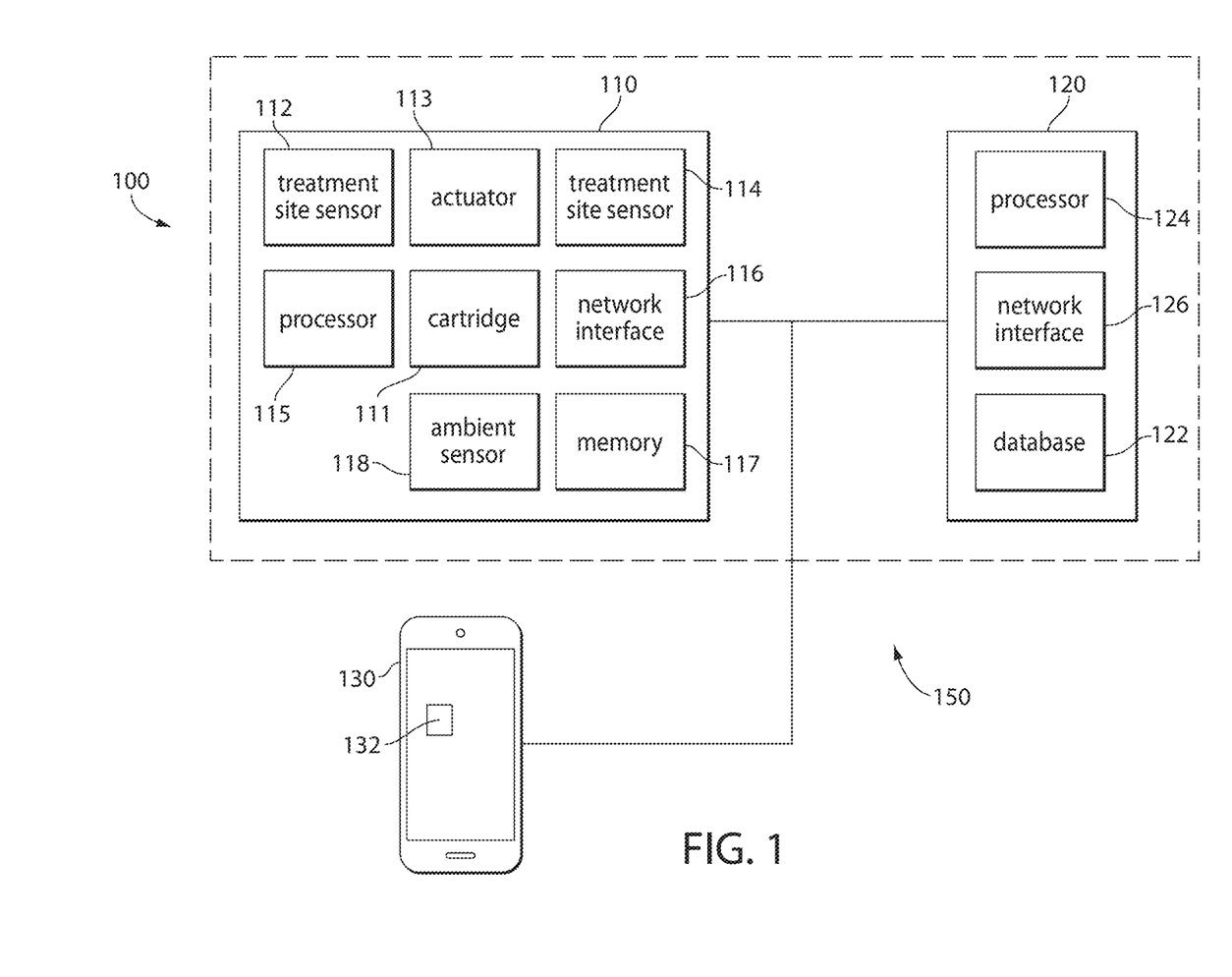
FIG. 1 is a block diagram of a connected health platform including a needle-free injector system according to one or more embodiments.

Aspects of the present disclosure relate to a medical device system that includes a medical treatment device, for example, a needle-based or needle-free injector such as an auto-injector, jet injector, or the like. FIG. 1 illustrates a block diagram of a connected health platform 150 including a needle-free injector system 100 according to one or more embodiments. In the embodiment shown in FIG. 1, the system 100 comprises an injector 110 in communication with a server 120. The server 120 and optionally the injector 110 are in communication with a user device 130 associated with a patient on a treatment regimen requiring use of the injector 100. The injector 110 collects compliance data to be provided to the server 120, which sends a message to the device 130 regarding the patient's compliance with the treatment regimen.

The injector 110 includes an actuator 113 controllable by a trigger or other input component (not shown) that delivers a needle-free subcutaneous jet injection of a medicine to the patient at a treatment site on the patient's body. In one embodiment, the actuator 113 is an electromagnetic actuator under computer feedback control, and is capable of delivering a 1 mL injection in less than 500 milliseconds. The medicine is provided in a cartridge 111 designed to be inserted into or otherwise connected to the injector 110, fluidly coupled in a manner that allows the medicine from cartridge 111 to be delivered subcutaneously by the actuator 113. In some embodiments, the cartridge 111 may contain one dose (e.g., a commonly-prescribed dosage amount) of the medicine; in other embodiments, the cartridge 111 may contain multiple doses, and so may be used for a number of injection treatments before being discarded. Embodiments of needle-free injectors of this type can be seen, for example, in U.S. patent application Ser. No. 14/490,126 (now U.S. Pat. No. 9,308,326), titled "Controlled Needle-Free Transport," filed on Sep. 18, 2014, which is incorporated by reference herein in its entirety.

In some embodiments, the injector 110 includes a conditioning element (not shown) for changing a temperature of the drug in the cartridge 111 prior to injection. For example, a heater or cooler may be disposed adjacent the cartridge 111 when it is inserted into the injector 110, and used to bring the medicine to within a defined temperature range to achieve, for example, a desired consistency or viscosity of the medicine.

The injector 110 also includes at least one treatment site sensor 112, 114 to detect one or more physiological parameters at the treatment site on the patient's body. For example, the at least one treatment site sensor 112, 114 may include a pressure sensor, a capacitive sensor, and/or a thermometer.

The injector 110 may be configured to use the at least one treatment site sensor 112, 114 to measure physiological parameters at the treatment site before, during, and/or after the treatment event. Such information may be used to determine compliance, or to allow, disallow, or modify a current or future treatment. For example, it may be known that a capacitance of the patient's skin at an injection site changes following an injection. Using the at least one treatment site sensor 112, 114 (e.g., at least one capacitive sensor) to detect a change in the capacitance of the patient's skin from before an injection event to after the injection event may provide an indication that the injection was successfully delivered. As another example, it may be known that temperature of the patient's skin at an injection site changes following an injection. Using the at least one treatment site sensor 112, 114 (e.g., at least one thermometer) to detect a change in the temperature of the patient's skin from before an injection event to after the injection event may provide an indication that the injection was successfully delivered.

The injector 110 may also include at least one ambient sensor 118 to detect an ambient or situational condition of the injector 110 at a time before, during, and/or after an injection event. In some embodiments, the at least one ambient sensor 118 includes at least one of an ambient thermometer, moisture sensor, gyroscope, or accelerometer. Information obtained via the at least one ambient sensor 118 may be used to determine compliance, or to allow, disallow, or modify a current or future treatment. For example, where the injector 110 is configured to deliver an injection in a generally vertical position, using the at least one ambient sensor 118 (e.g., at least one gyroscope) to determine that the injector 110 was substantially vertical at the time of the injection may provide an indication that the injection could be initiated and was successfully delivered. By contrast, determining that the injector 110 was generally horizontal may indicate that the medicine was delivered into the air (either inadvertently or not), and the injection was not successfully delivered. As another example, the at least one ambient sensor 118 (e.g., an accelerometer) may be used to determine if the injector 110 is moving at the time the patient triggers the injection. In some embodiments, the injector 110 may disallow the injection unless and until the injector 110 is substantially motionless, minimizing the risk of an inadvertently misdirected injection due to motion.

The at least one ambient sensor 118 may also include at least one sensor (e.g., a resistive touch sensor, a piezo touch sensor or switch, or a mechanical touch sensor) to detect an amount of pressure applied to the mechanism of the actuator 113 by the patient. Such information may be indicative of an intensity of pain being experienced by patients having certain conditions, such as rheumatoid arthritis, which can make applying a squeezing force by hand painful and difficult. In some embodiments, a sensitivity of the actuator 113 may be adjusted to account for the level of pressure detected by the sensor, such as by reducing the amount of effort needed to actuate the actuator 113 to administer a treatment.

In some embodiments, input from the at least one treatment site sensor 112, 114, the at least one ambient sensor 118, and/or other sensors may be used in combination to detect one or more conditions. For example, the at least one treatment site sensor 112, 114 may include a first contact sensor, and a second contact sensor may be disposed on or adjacent the handle of the injector 110. In combination, the first and second contact sensor may detect an electrical circuit that is formed through the user's body between the gripping hand and the treatment site. The existence of such a circuit can be used to confirm that the injection was administered into the patient's body.

Other sensors may be provided to detect conditions of the device, the injectate, and/or the treatment. In one example, the dosage size of individual treatments may be monitored by a sensor to confirm that a full dose was administered. In another example, injectate container pressure may be monitored to detect or predict an equipment malfunction. In still another example, the volume of injectate remaining in the cartridge of the injector 110 may be monitored by a sensor and used to request a refill of a prescription at the appropriate time. Other parameters or characteristics of the needle-free injector may also be monitored, including motion of the injector 110 before, during, and/or after an injection; the existence or amount of physical contact between the patient and the injector 110; and the existence or amount of positive contact force of the injector 110 to a contact surface of the patient.

The injector 110 also includes a processor 115 configured to initiate and/or control the operation of the actuator 113. The processor 115 may also receive the input from the at least one treatment site sensor 112, 114 and the at least one ambient sensor 118 and store the information in a memory 117 along with a time stamp or other metadata.

The injector 110 also includes a network interface 116 allowing for communication between the injector 110 and other systems or devices. The network interface may allow for communication via cell network (e.g., 3G or 4G), Wifi, Bluetooth, or other network communication protocol, and in some embodiments allows for wired communication between the injector 110 and other systems or devices.

In some embodiments, it may be desirable to make one or more components of a needle-free injector system disposable. For example, the injector 110 may include the actuator 113, the network interface 116, the at least one treatment site sensor 112, 114, and the at least one ambient sensor 118, but its functionality may be controlled by the user device 130, allowing for the inclusion of a processor 115 having reduced functionality and cost. The user device 130 may be paired with the injector 110, either wirelessly (e.g., Bluetooth) or by being communicatively coupled by a cable (e.g., USB). The injector 110 may stream data from the at least one treatment site sensor 112, 114, and the at least one ambient sensor 118 to the user device 130 for further processing and transmission to the server 120. An application on the user device 130 may provide an interface through which the patient can control the injector 110. In such embodiments, one or more doses of the drug may be provided in a unitary compartment on the injector 110, eliminating the need for the cartridge 111.

The server 120 includes a processor 124 and a network interface 126 that allows the server 120 to communicate with the injector 110, the user device 130, and other entities, as will be discussed in more detail below. In some embodiments, the injector 110 transmits information to the server 120 regarding the injector 110 and/or injection events. Such information may include, for example, the date, time, and duration of an injection event; software or firmware updates applied to the injector 110; data collected from the at least one treatment site sensor 112, 114 or the at least one ambient sensor 118; or other information. The server 120 may be configured or operated by any number of entities, including the manufacturer or seller of the injector 110, or the patient's healthcare professional, hospital, or payer.

The network interface 126 is configured to communicate with the user device 130, which may be a smart phone, tablet, PDA, computer, land line phone, or other mobile device associated with the patient. In some embodiments, the user device 130 is a dedicated mobile device provided to the patient along with the injector 110, and used primarily as part of the methods and systems described herein. The user device 130 may be a device owned or leased by the patient, or may be a device owned or leased by another person or entity having some association with the patient. For example, the user device 130 may be a device of someone associated with the patient, such as a caregiver, family member, neighbor, or friend. Information about the user device 130 may be provided, updated, and/or customized by the patient or others. In some embodiments, multiple user devices 130 may be identified, to be contacted according to various criteria including compliance goals. Escalating criteria may be set. For example, a patient meeting compliance goals may receive notifications on the patient's mobile device. Where the patient consistently fails to meet compliance goals for some period of time (e.g., a week), notifications may also be sent to members of the patient's family, as well as the patient's healthcare professional.

Compliance information may be reported to a central server for analysis and/or to be relayed to a medical professional, pharmacy, medical insurance company, or the like. The effectiveness of compliance-seeking interventions by the tracking device may also be tracked by the tracking device and/or a server. For example, a patient's compliance with a treatment regimen, either for a specific treatment event or over a number of treatment events spanning a period of time, may be compared to any interventions required during that time period. The effectiveness of the intervention in improving compliance may therefore be estimated or measured.

In some embodiments, one or more components of the system 100 may be configured to track the patient's level of compliance in association with the intervention actions (i.e., the notifications, reminders, and other communications or other intervention techniques) that resulted in the level of compliance. Actions that resulted in higher compliance may be identified and given higher priority for that patient or similarly-situated patients (e.g., patients in the same demographic) in the future. For example, if it is determined that a patient failed to comply after receiving emails and text message reminders to administer a treatment, but complied after receiving a voice message, the system 100 may cause that patient to receive voice messages in the first instance. Similarly, if it is determined that elderly patients are more likely to respond to a vibrating alarm on a mobile device than to a text message, the system 100 may suggest that current or newly-enrolled patients sign up to receive reminders in association with vibrating alarms, or may make such vibrating alarms the default setting for elderly patients.

In some embodiments, an outcome database (not shown) may be provided for compliance information to allow for data mining or other analysis of compliance and outcome information to determine ways to improve outcomes. For example, patients receiving different treatments may have a number of similar characteristics (e.g., symptoms, biographical information, behavioral attributes) that can be identified in the central outcome database. Intervention actions that were particularly effective with patients receiving one type of treatment may be explored with patients receiving another type of treatment if such similar characteristics are present.

The server 120 is configured to transmit to the user device 130 some information regarding the patient's treatment regimen and/or compliance in following it. For example, the server 120 may remind the patient via the user device 130 that the patient has missed a scheduled treatment, and may provide instructions for addressing the situation. As another example, the server 120 may send a message to the patient via the user device 130 providing encouragement, such as "KEEP UP THE GOOD WORK!" As still another example, the server 120 may send a message to the patient via the user device 130 with statistics such as overall compliance rate, on-time compliance rate, comparison of compliance rates during different time periods, comparison of the patient's compliance rate with the aggregate compliance rate of other patients, and other information that may be useful in increasing compliance rates and improving outcomes of treatment.

In some embodiments, the server 120 may be in communication with an application ("app") 132 on the user device 130. The app 132 may be configured to receive information from the server 120 and to generate messages, actions, data, views, summaries, detailed views, or the like, relating to the patient's compliance with a treatment regimen. For example, the app 132 may provide a dashboard view of the patient's treatment schedule, as well as the patient's compliance level, for a given period of time (e.g., the previous 7 days). In some embodiments, the app 132 may have the necessary permissions from the patient or another user to take additional action. For example, the app 132 may receive a notification from the server 120 regarding the patient's compliance level, and in response may set a reminder using a calendar application of the user device 130 alerting the patient at a suitable time to perform an injection. As another example, the app 132 may receive a notification from the server 120 regarding the patient's compliance level, and in response may arrange a call between the patient and a healthcare professional, call center, or other participant to discuss any issues with compliance.

The app 132 may interact with other applications running on the user device 130 to obtain additional data relating to the patient's health and/or compliance with the treatment regimen. For example, information about the patient's diet, weight, activity level, or mood may be obtained from other applications running on the user device 130 by accessing data associated with the other applications, or by passing or receiving requests from an application programming interface (API). The app 132 may also interact with cloud-based applications having data associated with the patient, such as social networks or health/fitness monitoring platforms (e.g., the MyFitnessPal application offered by Under Armour of Baltimore, Md.).

Figure 3:
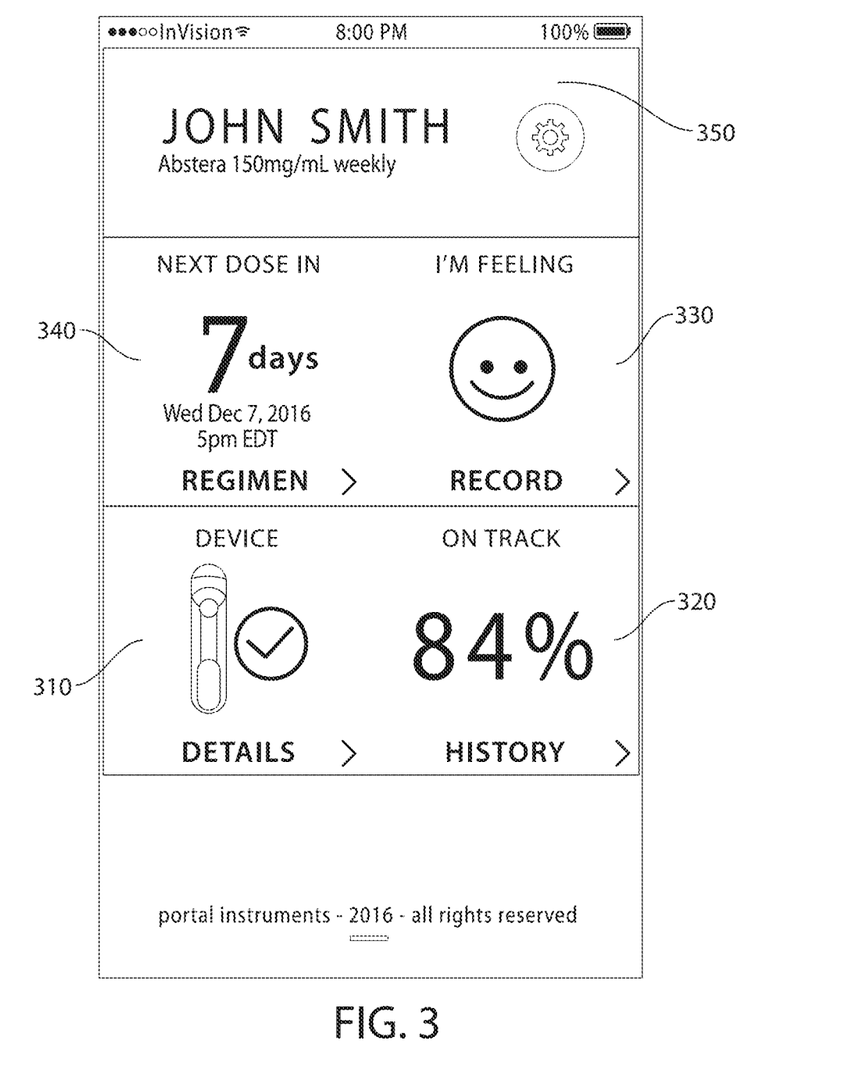
FIG. 3 is an illustration of a user interface displayed by a needle-free injector system according to one or more embodiments.

In some embodiments, the user device 130 presents a "dashboard" or overview interface providing information about the patient's past and upcoming treatments, as well as the patient's compliance with past treatments. An example overview interface 300 is shown in FIG. 3. The overview interface 300 may provide an injector status icon 310 indicating the current status of the injector 110, such as "ACTIVE", "POWERED OFF", "CHARGING", etc. The overview interface 300 may also provide a compliance icon 320 indicating the patient's recent compliance statistics (e.g., a percentage of the injection events in the past 7 days with which the patient was compliant). Selecting the compliance icon 320 may present a more detailed view of the patient's compliance over various selectable periods of time. The overview interface 300 may also provide a mood icon 330, indicating the patient's current wellness. Selecting the mood icon 330 may present a more detailed view in which the patient can view, modify, or provide feedback on such factors as pain level, symptoms, sleep amount, or emotional state. The overview interface 300 may also provide a next treatment icon 340, showing the date and time of the patient's next scheduled injection. Selecting the next treatment icon 340 may present the patient with a more detailed schedule of upcoming injections, and may allow the schedule to be modified in some aspects. For example, where a patient has a scheduled commitment at the time of an upcoming injection, it may be possible to delay or accelerate the scheduled injection by some amount of time. The schedule for prior or subsequent injections may also be modified to compensate for any such changes. As another example, when a patient receives a reminder that it is time to perform an injection, the overview interface 300 may provide the patient with a limited number of opportunities to delay the injection until a more convenient time by resetting the reminder for some time in the future, such as by hitting a "snooze" button.

The overview interface 300 may also provide such basic information 350 as the patient's name, drug, regimen (e.g., "bi-weekly"), and start date of the current regimen. The overview interface 300 may also provide a contact icon (not shown) that, when selected, provides the patient with connectivity to a healthcare professional, manufacturer of the device, community forum, or others. The overview interface 300 may also provide an instruction icon (not shown) allowing the patient to access and review instructions and indications for the treatment regimen.

Referring again to FIG. 1, in some embodiments, information about the patient and the user device 130 may be stored by the server 120 and used to deliver messages to the user device 130. For example, the server 120 may store a phone number of the user device 130, along with information indicating that the user device 130 is a mobile phone, and may send a message to the user device 130 in the form of an SMS message. In another example, the server 120 may store a phone number of the user device 130, along with information indicating that the user device 130 is a conventional landline phone, and may send a message to the patient in the form of a prerecorded voice message delivered by telephone. In other embodiments, the server 120 may store contact information for the patient or an associated individual or entity (e.g., phone number, email address, etc.) without regard to the characteristics of the user device 130. For example, the patient may provide an email address allowing the server 120 to send a communication to the patient or other person. While the message may be retrieved, from the account associated with the email address, using the user device 130, the server 120 may not know the identity of the user device 130 at the time the message was sent.

The server 120 further includes a database 122 configured to store data and metadata about the injector 110. In some embodiments, the database 122 stores data and metadata about events relating to the injector 110. For example, the database 122 may include fields such as datetime, type of event, status, and one or more event values associated with the event. Where the type of event is "INJECTION", the status may be "SUCCESS", and the event values may describe characteristics of the injection, such as its duration, actuator speed, etc.

Figure 2:
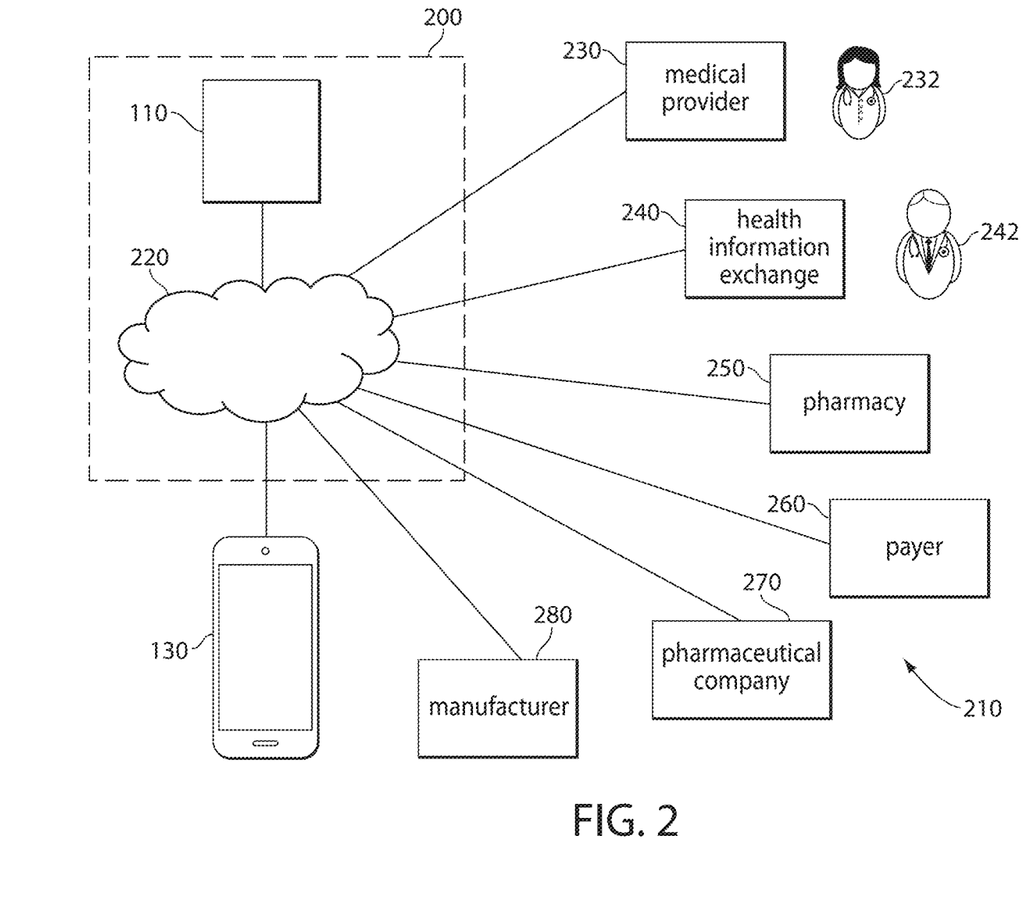
FIG. 2 is a block diagram of other aspects of the connected health platform of FIG. 1 according to one or more embodiments.

The server 120 may be further configured to communicate compliance or other information with other systems, individuals, or entities via the network interface 126. For example, a needle-free injection system 200 may be configured to communicate with other systems involved in the patient's treatment regimen. FIG. 2 illustrates a block diagram of a connected health platform 210 including a needle-free injector system 200 and a number of third-party systems according to one or more embodiments. In these embodiments, the injector 110 and the user device 130 communicate with a cloud computing network 220 that may include one or more servers (not shown) similar to server 120 in needle-free injector system 100 previously shown in FIG. 1. The cloud computing network 220 may also allow for communication with one or more third parties. The communication may include compliance information, on a detailed (e.g., injection-level) basis, or in the aggregate. The communication may also include information about the needle-free injector system 200, including the function and status of the injector 110. The communication may be performed over email or other messaging format, may be performed through an API call, or may include uploading or otherwise transmitting formatted data to be stored in a database or other data store by the one or more third parties.

In some embodiments, the needle-free injector system 200 can communicate with a medical provider 230 and/or a health information exchange 240. For example, the medical provider 230 may be a community or private hospital, a VA hospital, a medical practice of one or more physicians or other healthcare professionals, a clinic, or other entity through which physicians 232, 242 or other healthcare providers offer healthcare services to the patient. The needle-free injector system 200 may communicate to the medical provider 230 to receive information about the patient including the patient's age, gender, medical conditions, and currently prescribed and/or contraindicated medications. In some embodiments, the needle-free injector system 200 may receive the patient's electronic medical record from the medical provider 230.

The needle-free injector system 200 may communicate to the medical provider 230 regarding the patient's compliance in administering one or more recent injections. The compliance information may include the scheduled time of the most recent injection, as well as the time that the injection was actually administered, if any; the amount of drug administered; and data gathered from the at least one treatment site sensor 112, 114 and/or the at least one ambient sensor 118. The information from the at least one treatment site sensor 112, 114 and/or the at least one ambient sensor 118 may be used to determine if the patient complied with the treatment regimen or, if not, possible reasons why. For example, where the at least one ambient sensor 118 includes a moisture sensor, information about the moisture/humidity in the air at the time of a scheduled injection may be sent to the medical provider 230. For some conditions, including rheumatoid arthritis, the patient may experience higher levels of discomfort at higher moisture levels. An indication that the patient did not administer a recently scheduled injection at a time of relatively high humidity may suggest that the patient was experiencing joint pain in the hand that interfered with use of the injector 110. When such issues are detected, solutions or suggestions may be provided to the patient to increase compliance.

The needle-free injector system 200 may make compliance information available to the medical provider 230 by making the information available for download, or by email, FAX, or by transmitting an electronic medical record or portions thereof. The information may be incorporated into the medical records for the patient maintained by the medical provider 230. In some embodiments, the information is provided to the medical provider 230 periodically, such as hourly, daily, weekly, or monthly, or when defined events have occurred (such as a missed treatment event). In other embodiments, the medical provider 230 may be given the opportunity to receive compliance information about the patient on demand or at a requested time, such as by email, download, or FAX. Such an option may be useful in allowing the medical provider 230 to have the most up-to-date information before an appointment with the patient.

In some embodiments, the needle-free injector system 200 may track the patient's medical outcome in association with the compliance and other information provided to the medical provider 230. For example, it may be determined that a patient achieves a more optimal outcome when certain compliance information (such as the nature of the treatment or the frequency of administration of treatments) is highlighted for the medical provider 230, allowing the medical provider 230 to more readily identify ongoing issues with the treatment or compliance therewith.

In some embodiments, the needle-free injector system 200 can communicate with a pharmacy 250 or other provider of drugs (e.g., packaged in one or more cartridges 111, FIG. 1). For example, by receiving notifications about the number of injections administered by the patient, the needle-free injector system 200 may track the number of doses remaining in the patient's possession. When the number of remaining doses falls below a certain threshold, or if the medication has expired, the needle-free injector system 200 may communicate a refill order to the pharmacy 250.

In some embodiments, the needle-free injector system 200 can communicate with a payer 260, such as a health insurance company. For example, detailed and/or aggregate compliance information may be transmitted to the payer 260 to allow the payer 260 to confirm that the treatments being paid for are being properly administered.

In some embodiments, the needle-free injector system 200 can communicate with a pharmaceutical company 270 that manufactures and/or markets the drug being administered during the treatment regimen. Compliance information may also be provided, along with outcome/treatment information (e.g., in an anonymized format). Such information may allow the pharmaceutical company 270 to tailor certain characteristics of the drug (e.g., molecule size) to improve compliance and outcomes.

In some embodiments, the needle-free injector system 200 can communicate with a manufacturer 280 of the injector 110, or other entity responsible for the function of the injector 110. For example, information about the injection profile (including the velocity and duration of the injection) may be provided to the manufacturer 280. Information about the injector 110 may also be transmitted to the manufacturer 280 to detect any problems with the injector 110, or to schedule maintenance or replacement of the injector 110. For example, the injector 110 may be configured to periodically perform self-tests of its functionality (e.g., the velocity of the actuator 113) and to report the results of such tests to the manufacturer 270. Other information may be transmitted to the manufacturer 280, including information about battery charge/battery life and injection profiles. If the information sent to the manufacturer 280 indicates that the injector's performance has degraded beyond a certain point, arrangements may be made to replace the injector 110 or components thereof.

In some embodiments, compliance information may be made available to the patient or third parties in the form of a dashboard view. The dashboard view may present information about a single patient, or aggregated information about multiple patients, in a configurable format. For example, a dashboard may be presented to a medical provider 230, a health information exchange 240, a pharmacy 250, a payer 260, a pharmaceutical company 270, or a manufacturer 280. The dashboard may be configurable to display information relevant to any of those third parties. For example, the dashboard may display (in text and/or graphics) the reasons given by patients for missed doses for one or more patients during a particular time period; the rate of compliance for a given period; the effectiveness of various intervention actions taken during a given time period, in terms of successful treatments that would likely have been otherwise missed; and the number of sequential treatments administered by patients during a time period (e.g., number of patients administering a third dose of a course of treatment during a given month).

Figure 4:
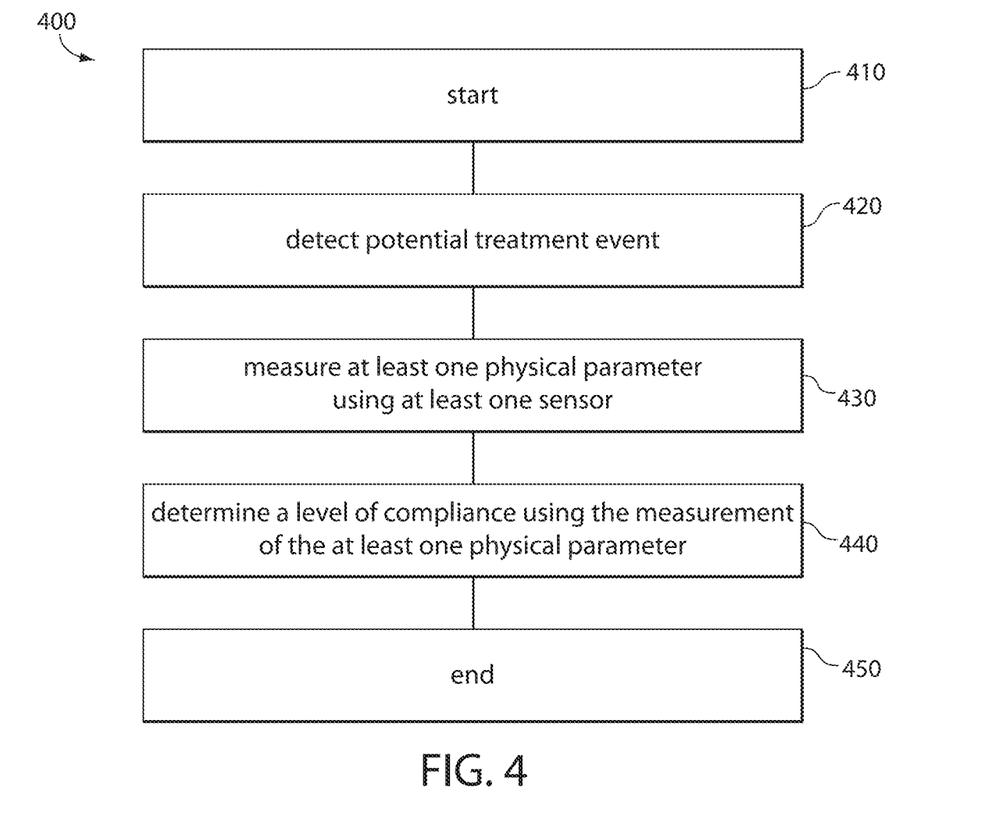
FIG. 4 is a flow chart of a method for determining patient compliance with a treatment regimen according to one or more embodiments.

FIG. 4 is a flow chart of a process 400 for determining patient compliance with a treatment regimen according to one or more embodiments. Such embodiments may be implemented using a system such as those illustrated in FIGS. 1 and 2.

The process 400 begins at step 410.

Figure 5A:
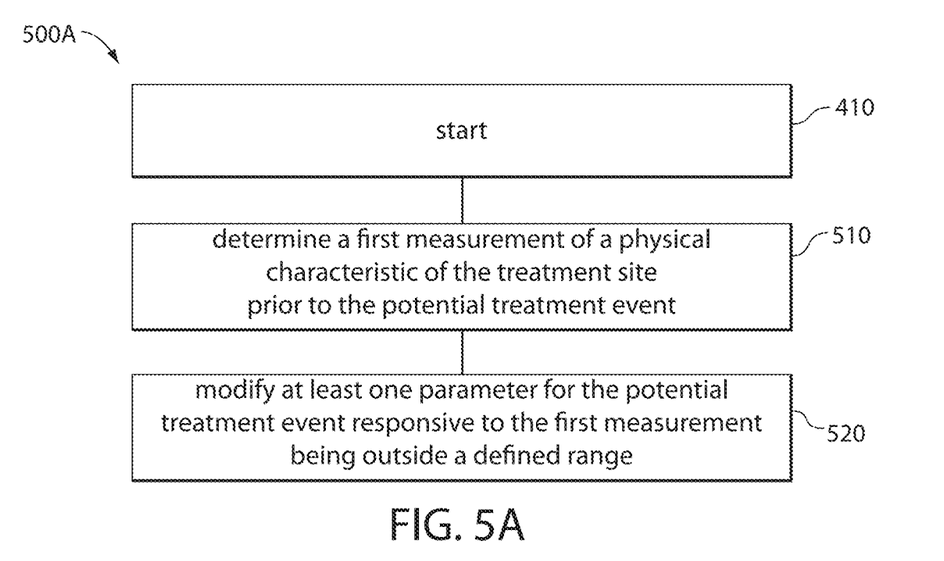
FIGS. 5A-5D are flow charts of additional steps that may be performed in embodiments of the method illustrated in FIG. 4.

In some embodiments, as can be seen in FIG. 5A, a subprocess 500A may be performed. At step 510, a first measurement of a physical characteristic of the treatment site is determined prior to a potential treatment event, and at step 520, at least one parameter of the potential treatment event is modified responsive to the first measurement being outside a defined range. For example, the first measurement may detect that the patient's skin at the treatment site has a relatively high temperature, which may make it more compliant to a subcutaneous injection. In response, one or more parameters (e.g., actuator velocity) may be adjusted to compensate for the temperature reading being above a defined range. In some embodiments, the injection may be disallowed where the first measurement is outside of a defined range. For example, where the temperature reading of the patient's skin indicates that the patient has a fever, and administering the injection is contraindicated, the actuator may be disabled until an acceptable temperature reading is subsequently obtained.

Returning to FIG. 4, at step 420, a potential treatment event by a needle-free injector system is detected. For example, the injector may detect that the actuator has deployed a dose of the drug, indicating that a potential treatment event has occurred—i.e., the drug has either been injected into the patient during a treatment event, or deployed elsewhere. The potential treatment event may be detected via an event log entry for the potential treatment event, or by a hardware interrupt or system flag being set.

Figure 5B:
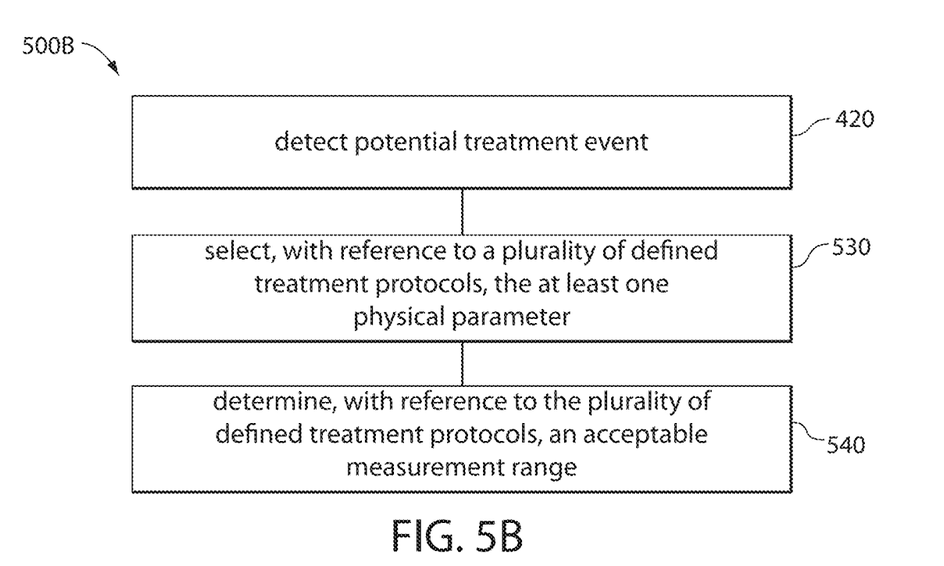

In some embodiments, as can be seen in FIG. 5B, a subprocess 500B may be performed. At step 530, at least one physical parameter is selected with reference to a plurality of defined treatment protocols, and at step 540, an acceptable measurement range may be determined with reference to the plurality of defined treatment protocols. The plurality of defined treatment protocols may identify at least one physical parameter, and a measurement range over which compliance may be determined to occur. Each protocol in the plurality of defined treatment protocols may correspond to a disorder, and may identify physical parameters and associated acceptable measurement ranges relevant to the disorder. For example, a defined treatment protocol may indicate that a physiological reaction to the injection will cause the temperature of the treatment site to rise by an amount in the range of 1-2 degrees Fahrenheit.

Returning again to FIG. 4, at step 430, at least one physical parameter is measured using at least one sensor proximal to the treatment site on the body of the patient. As discussed above with respect to FIGS. 1 and 2, the at least one physical parameter may include, for example, the capacitance or temperature of the patient's skin, or inflammation of the patient's skin.

According to some embodiments, the at least one physical parameter to be measured is selected according to a defined treatment protocol. A plurality of defined treatment protocols may be accessible by the injector, and one of the defined treatment protocols may be selected based on the specific disorder, or disorder type, for which the patient is being treated. The defined treatment protocol may indicate which physical parameters should be measured (i.e., which sensors should be used), and may include such information as the timing and duration of the measurement, as well as what constitutes an acceptable range for the measurement.

At step 440, a level of compliance of the patient is determined using the measurement of the at least one physical parameter. As discussed above with respect to FIGS. 1 and 2, the patient's compliance may be determined by analyzing the at least one physical parameter, or comparing it to a reading of the physical parameter prior to the injection. For example, detecting a change in temperature of the patient's skin near the treatment site from before and after the potential treatment event may indicate that the patient is having a (possibly normal) physiological reaction to the injection event, meaning the potential injection event may be an actual injection event. The level of compliance may be determined by the injector (e.g., injector 110) and/or a server (e.g., server 120), either alone or in combination. In some embodiments, the level of compliance may expressed as either "COMPLIANT" or "NON-COMPLIANT." In other embodiments, the level of compliance may be expressed as a percentage (e.g., the patient successfully delivered 87% of a dose of the drug during the potential injection event). In some embodiments, the level of compliance may be stated for a period of time (e.g., a day, a week, a month, or a year) or for a given number of scheduled treatment events. Compliance may be stated in this manner in order to encourage the patient, and the manner of expressing compliance may be selected based on the effect prior characterizations of compliance had on subsequent compliance. For example, statements of compliance may be in the format of "the patient has been compliant for 9 weeks" or "the patient's compliance with the prescribed therapy is 87%."

Figure 5C:
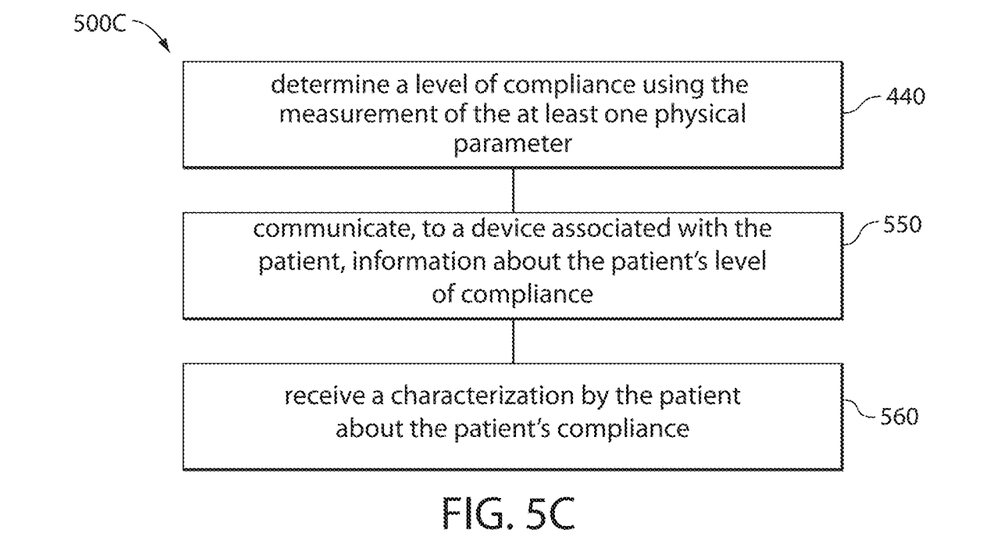

In some embodiments, as can be seen in FIG. 5C, a subprocess 500C may be performed. At step 550, information about the patient's level of compliance is communicated to a device associated with the patient (e.g., the patient smartphone or tablet device). For example, the patient may be notified that a scheduled injection was missed, and may be asked questions to determine a reason for the missed treatment. For example, the patient may be asked "DID YOU FORGET?" At step 560, a characterization is received from the patient regarding the patient's compliance. For example, the patient may be provided the option to answer "YES" to the question "DID YOU FORGET?"

Figure 5D:
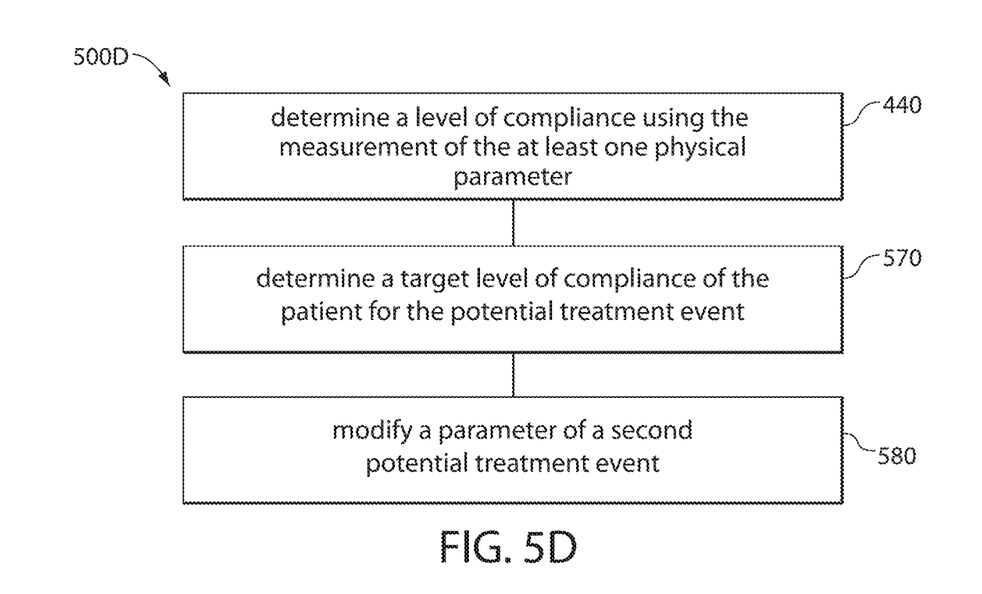

In other embodiments, as can be seen in FIG. 5D, a subprocess 500D may be performed. A level of compliance of the patient may be determined for a plurality of potential treatment events. At step 570, a target level of compliance of the patient is determined for the potential treatment event. For example, it may be determined that the patient is to receive some total amount of medicine over a 24 hour period. At step 580, a parameter of a second potential treatment event is modified based on the level of compliance of the patient for the plurality of potential treatment events, and on the target level of compliance of the patient determined at step 570. For example, if it is determined that the patient has received, on average, less than an entire dose of medicine during previous treatment events, some parameter (e.g., actuator velocity) may be modified for a second potential treatment event in order to improve compliance.

Returning again to FIG. 4, the process 400 ends at step 450.

As discussed above, aspects and functions disclosed herein may be implemented as hardware or software on one or more of these computer systems. There are many examples of computer systems that are currently in use. These examples include, among others, network appliances, personal computers, workstations, mainframes, networked clients, servers, media servers, application servers, database servers and web servers. Other examples of computer systems may include mobile computing devices, such as cellular phones and personal digital assistants, and network equipment, such as load balancers, routers and switches. Further, aspects may be located on a single computer system or may be distributed among a plurality of computer systems connected to one or more communications networks.

For example, various aspects and functions may be distributed among one or more computer systems configured to provide a service to one or more client computers. Additionally, aspects may be performed on a client-server or multi-tier system that includes components distributed among one or more server systems that perform various functions. Consequently, examples are not limited to executing on any particular system or group of systems. Further, aspects may be implemented in software, hardware or firmware, or any combination thereof. Thus, aspects may be implemented within methods, acts, systems, system elements and components using a variety of hardware and software configurations, and examples are not limited to any particular distributed architecture, network, or communication protocol.

The computer devices described herein are interconnected by, and may exchange data through, a communication network. The network may include any communication network through which computer systems may exchange data. To exchange data using the network, the computer systems and the network may use various methods, protocols and standards, including, among others, Fibre Channel, Token Ring, Ethernet, Wireless Ethernet, Bluetooth, IP, IPV6, TCP/IP, UDP, DTN, HTTP, FTP, SNMP, SMS, MMS, SS7, JSON, SOAP, CORBA, REST and Web Services. To ensure data transfer is secure, the computer systems may transmit data via the network using a variety of security measures including, for example, TSL, SSL or VPN.

The computer systems include processors that may perform a series of instructions that result in manipulated data. The processor may be a commercially available processor such as an Intel Xeon, Itanium, Core, Celeron, Pentium, AMD Opteron, Sun UltraSPARC, IBM Power5+, or IBM mainframe chip, but may be any type of processor, multiprocessor or controller.

A memory may be used for storing programs and data during operation of the device. Thus, the memory may be a relatively high performance, volatile, random access memory such as a dynamic random access memory (DRAM) or static memory (SRAM). However, the memory may include any device for storing data, such as a disk drive or other non-volatile storage device. Various examples may organize the memory into particularized and, in some cases, unique structures to perform the functions disclosed herein.

The devices (e.g., the user device 130) may also include one or more interface devices such as input devices and output devices. Interface devices may receive input or provide output. More particularly, output devices may render information for external presentation. Input devices may accept information from external sources. Examples of interface devices include keyboards, mouse devices, trackballs, microphones, touch screens, printing devices, display screens, speakers, network interface cards, etc. Interface devices allow the computer system to exchange information and communicate with external entities, such as users and other systems.

Data storage may include a computer readable and writeable nonvolatile (non-transitory) data storage medium in which instructions are stored that define a program that may be executed by the processor. The data storage also may include information that is recorded, on or in, the medium, and this information may be processed by the processor during execution of the program. More specifically, the information may be stored in one or more data structures specifically configured to conserve storage space or increase data exchange performance. The instructions may be persistently stored as encoded signals, and the instructions may cause the processor to perform any of the functions described herein. The medium may, for example, be optical disk, magnetic disk or flash memory, among others. In operation, the processor or some other controller may cause data to be read from the nonvolatile recording medium into another memory, such as the memory, that allows for faster access to the information by the processor than does the storage medium included in the data storage. The memory may be located in the data storage or in the memory, however, the processor may manipulate the data within the memory, and then copy the data to the storage medium associated with the data storage after processing is completed. A variety of components may manage data movement between the storage medium and other memory elements and examples are not limited to particular data management components. Further, examples are not limited to a particular memory system or data storage system.

Various aspects and functions may be practiced on one or more computers having a different architectures or components than that shown in the Figures. For instance, one or more components may include specially programmed, special-purpose hardware, such as for example, an application-specific integrated circuit (ASIC) tailored to perform a particular operation disclosed herein. While another example may perform the same function using a grid of several general-purpose computing devices running MAC OS System X with Motorola PowerPC processors and several specialized computing devices running proprietary hardware and operating systems.

One or more components may include an operating system that manages at least a portion of the hardware elements described herein. A processor or controller may execute an operating system which may be, for example, a Windows-based operating system, such as, Windows NT, Windows 2000 (Windows ME), Windows XP, Windows Vista or Windows 7 operating systems, available from the Microsoft Corporation, a MAC OS System X operating system available from Apple Computer, an Android operating system available from Google, one of many Linux-based operating system distributions, for example, the Enterprise Linux operating system available from Red Hat Inc., a Solaris operating system available from Sun Microsystems, or a UNIX operating systems available from various sources. Many other operating systems may be used, and examples are not limited to any particular implementation.

The processor and operating system together define a computer platform for which application programs in high-level programming languages may be written. These component applications may be executable, intermediate, byte-code or interpreted code which communicates over a communication network, for example, the Internet, using a communication protocol, for example, TCP/IP. Similarly, aspects may be implemented using an object-oriented programming language, such as .Net, SmallTalk, Java, C++, Ada, or C # (C-Sharp). Other object-oriented programming languages may also be used. Alternatively, functional, scripting, or logical programming languages may be used.

Additionally, various aspects and functions may be implemented in a non-programmed environment, for example, documents created in HTML, XML or other format that, when viewed in a window of a browser program, render aspects of a graphical-user interface or perform other functions. Further, various examples may be implemented as programmed or non-programmed elements, or any combination thereof. For example, a web page may be implemented using HTML while a data object called from within the web page may be written in C++. Thus, the examples are not limited to a specific programming language and any suitable programming language could be used. Thus, functional components disclosed herein may include a wide variety of elements, e.g. executable code, data structures or objects, configured to perform described functions.

What is claimed is:

1. A needle-free injector system comprising:
a needle-free injector configured to deploy a dose of a treatment to a patient as an injection event;
a gyroscope configured to monitor an orientation of the needle-free injector during the injection event;
a first contact sensor configured to detect electric current at a treatment site on the patient;
a second contact sensor configured to detect electric current adjacent a handle of the needle-free injector; and
a processor configured to perform steps of:
detecting that an actuator of the needle-free injector has deployed the dose in the injection event;
monitoring a signal from the gyroscope during the injection event;
determining an orientation of the needle-free injector during the injection event based on the signal from the gyroscope;
detecting an electrical circuit formed through the first contact sensor, the second contact sensor, and the patient's body during the injection event;
determining whether the injection event was a treatment event including a successful delivery of the dose to the patient based on the orientation of the needle-free injector during the injection event and the existence or non-existence of the electrical circuit during the injection event; and
transmitting information regarding the injection event to a server.

2. The needle-free injector system of claim 1, the processor further configured to perform steps of:
determining a likelihood that the dose of the treatment was successfully delivered to the patient; and
transmitting the likelihood to the server.

3. The needle-free injector system of claim 1, wherein the server comprises a processor configured to perform steps of:
receiving, at the server, information for a plurality of treatment events for the patient over a period of time, the information indicating a degree to which the patient has administered the plurality of treatment events;
determining a compliance rate for a treatment regimen of the patient for the plurality of treatment events; and
communicating, to a device associated with the patient, a message regarding an administration of at least one of the plurality of treatment events.

4. The needle-free injector system of claim 1, wherein the processor is further configured to perform steps of:
determining that the injection event was not a treatment event including a successful delivery of the dose to the patient; and
transmitting a notification to at least one of a device of the patient and a device of a caregiver of the patient.

5. The needle-free injector system of claim 1, wherein the processor is further configured to perform steps of:
determining that the injection event was not a treatment event including a successful delivery of the dose to the patient; and
presenting the patient with instructions regarding the injection event.

6. The needle-free injector system of claim 1, wherein the processor is further configured to perform steps of:
determining, based on the signal from the at least one ambient sensor during the injection event, that there is a low likelihood that the dose of the treatment was successfully delivered to the patient, and
presenting the patient with instructions regarding the injection event.

7. A needle-free injector system comprising:
a needle-free injector having at least one ambient sensor configured to monitor an ambient condition of the needle-free injector;
a first contact sensor configured to detect contact with a treatment site on a patient;
a second contact sensor configured to detect electric current adjacent a handle of the needle-free injector; and
a processor configured to perform steps of:
detecting that an actuator of the needle-free injector has deployed a dose of a treatment as an injection event;
monitoring a signal from the at least one ambient sensor during the injection event;

detecting, based on a signal from the first contact sensor and the second contact sensor, a contact with the patient during the injection event;

determining, based on the signal from the at least one ambient sensor during the injection event and the signal from the first contact sensor indicating whether the needle-free injector was in contact with patient, a likelihood that the dose of the treatment was successfully delivered to the patient; and transmitting information to a server regarding the injection event.

8. The needle-free injector system of claim 7, wherein transmitting information to the server includes transmitting an indication of whether the injection event was successful.

9. The needle-free injector system of claim 7, wherein the server comprises a server configured to:

receive, for a plurality of treatment events over a period of time, a degree to which the patient has administered the plurality of treatment events;

determine a compliance rate for a treatment regimen of the patient for the plurality of treatment events; and communicate, to a device associated with the patient, a message regarding an administration of at least one of the plurality of treatment events.

10. The needle-free injector system of claim 9, wherein the server is configured to allow, disallow, or modify a current or future treatment based on the compliance rate.

11. The needle-free injector system of claim 7, wherein the at least one ambient sensor includes a gyroscope.

12. The needle-free injector system of claim 11, wherein the processor is configured to deliver the dose at a predetermined orientation of the needle-free injector based on the signal from the gyroscope.

13. The needle-free injector system of claim 7, wherein the at least one ambient sensor includes an accelerometer.

14. The needle-free injector system of claim 13, wherein the processor is configured to disallow the injection event unless the needle-free injector is substantially motionless based on the signal from the accelerometer.

15. The needle-free injector system of claim 7, wherein the at least one ambient sensor includes a capacitive sensor.

16. The needle-free injector system of claim 15, wherein the processor is configured to detect a successful delivery of the dose to the patient based on a change in a skin capacitance of the patient from before the injection event to after the injection event.

17. The needle-free injector system of claim 7, wherein the at least one ambient sensor include a thermometer.

18. The needle-free injector system of claim 17, wherein the processor is configured to detect a successful delivery of the dose to the patient based on a change in a skin temperature of the patient from before the injection event to after the injection event.

19. The needle-free injector system of claim 7, wherein the ambient condition includes an orientation of the needle-free injector.

20. The needle-free injector system of claim 19, wherein the needle-free injector is configured to deliver an injection in a vertical orientation, and wherein a substantially horizontal orientation detected by the ambient sensor during the injection event indicates that the injection was not successful.

21. The needle-free injector system of claim 19, wherein the needle-free injector is configured to deliver an injection in a vertical orientation, wherein a substantially vertical orientation detected by the ambient sensor during the injection event indicates that the injection was successful.

22. The needle-free injector system of claim 7, wherein the ambient condition includes an absence of motion of the needle-free injector during the injection event.

23. The needle-free injector system of claim 7, wherein the processor is further configured to perform steps of:

determining, based on the signal from the at least one ambient sensor during the injection event, that there is a low likelihood that the dose of the treatment was successfully delivered to the patient, and transmitting a notification to at least one of a device of the patient and a device of the patient's caregiver.

* * * * *

UNITED STATES PATENT AND TRADEMARK OFFICE
CERTIFICATE OF CORRECTION

PATENT NO. : 11,896,805 B2
APPLICATION NO. : 16/823043
DATED : February 13, 2024
INVENTOR(S) : Mark Philip, Patrick Armand Anquetil and Ian Hunter Page 1 of 1

It is certified that error appears in the above-identified patent and that said Letters Patent is hereby corrected as shown below:

In the Claims

In Column 22, Line 38, Claim 23, delete "a device of the patient's caregiver" and insert -- a device of a caregiver of the patient --.

Signed and Sealed this
Sixth Day of May, 2025

Coke Morgan Stewart
*Acting Director of the United States Patent and Trademark Office*